United States Patent
Marik et al.

(10) Patent No.: US 9,504,480 B2
(45) Date of Patent: Nov. 29, 2016

(54) METHODS AND INSTRUMENTS FOR USE IN VERTEBRAL TREATMENT

(71) Applicant: Warsaw Orthopedic, Inc., Warsaw, IN (US)

(72) Inventors: Greg C. Marik, Collierville, TN (US); Newton H. Metcalf, Jr., Memphis, TN (US); Danish Siddiqui, Collierville, TN (US); Vincent C. Traynelis, Chicago, IL (US)

(73) Assignee: Warsaw Orthopedic, Inc., Warsaw, IN (US)

(*) Notice: Subject to any disclaimer, the term of this patent is extended or adjusted under 35 U.S.C. 154(b) by 0 days.

(21) Appl. No.: 14/617,283

(22) Filed: Feb. 9, 2015

(65) Prior Publication Data
US 2015/0272595 A1 Oct. 1, 2015

Related U.S. Application Data

(62) Division of application No. 13/098,026, filed on Apr. 29, 2011, now Pat. No. 8,998,905.

(51) Int. Cl.
*A61B 17/16* (2006.01)
*A61B 17/70* (2006.01)
*A61F 2/44* (2006.01)
*A61B 17/02* (2006.01)

(52) U.S. Cl.
CPC ......... *A61B 17/1671* (2013.01); *A61B 17/025* (2013.01); *A61B 17/16* (2013.01); *A61B 17/1659* (2013.01); *A61B 17/7064* (2013.01); *A61F 2/4405* (2013.01); *A61B 90/03* (2016.02); *A61B 2017/0256* (2013.01)

(58) Field of Classification Search
CPC .............. A61B 17/16; A61B 17/1659; A61B 17/1671; A61B 19/30
See application file for complete search history.

(56) References Cited

U.S. PATENT DOCUMENTS

| | | | |
|---|---|---|---|
| 4,625,725 A | * | 12/1986 | Davison ............. A61B 17/1659 407/29.1 |
| 5,741,261 A | | 4/1998 | Moskovitz et al. |
| 5,891,147 A | | 4/1999 | Moskovitz et al. |
| 6,287,313 B1 | | 9/2001 | Sasso |
| 6,485,518 B1 | | 11/2002 | Cornwall et al. |
| 6,562,046 B2 | | 5/2003 | Sasso |
| 6,579,319 B2 | | 6/2003 | Goble et al. |
| 6,949,123 B2 | | 9/2005 | Reiley |
| 7,041,136 B2 | | 5/2006 | Goble et al. |
| 7,074,238 B2 | | 7/2006 | Stinson et al. |

(Continued)

OTHER PUBLICATIONS

Goel, Atlantoaxial joint jamming as a treatment for a atlantoaxial dislocation: a preliminary report, Dept. of Neurosurgery, King Edward Memorial Hosp. and Seth Gordhandas Sunderdas Medical College, Parel, Mumbai, India, J. Neurosurg Spine 7:90-94, 2007.

(Continued)

*Primary Examiner* — Larry E Waggle, Jr.

(57) ABSTRACT

Embodiments of the invention include instruments, implants, and methods for surgically treating facet joints of vertebrae. An instrument may be advanced into one or more facet joints to one or both separate vertebrae and remove tissue from one or more articular processes. A stop on the instrument may be used to terminate advancement of the instrument by contacting a vertebra, and one or more implants may be placed into one or more facet joints.

18 Claims, 13 Drawing Sheets

(56) References Cited

U.S. PATENT DOCUMENTS

| | | | |
|---|---|---|---|
| 7,087,084 B2 | 8/2006 | Reiley | |
| 7,090,698 B2 | 8/2006 | Goble et al. | |
| 7,223,269 B2 | 5/2007 | Chappuis | |
| 7,445,635 B2 | 11/2008 | Fallin et al. | |
| 7,504,374 B2 | 3/2009 | Marx et al. | |
| 7,517,358 B2 | 4/2009 | Petersen | |
| 7,632,278 B2 * | 12/2009 | Jansen | A61B 17/1671 606/86 A |
| 7,708,761 B2 | 5/2010 | Petersen | |
| 7,833,247 B2 | 11/2010 | Sharim | |
| 7,846,183 B2 | 12/2010 | Blain | |
| 7,846,184 B2 | 12/2010 | Sasso et al. | |
| 7,922,766 B2 * | 4/2011 | Grob | A61B 17/1757 606/247 |
| 2002/0151895 A1 | 10/2002 | Soboleski et al. | |
| 2004/0049276 A1 | 3/2004 | Reiley | |
| 2004/0111093 A1 | 6/2004 | Chappuis | |
| 2004/0111154 A1 | 6/2004 | Reiley | |
| 2005/0010291 A1 | 1/2005 | Stinson | |
| 2005/0027361 A1 | 2/2005 | Reiley | |
| 2005/0159746 A1 | 7/2005 | Grob | |
| 2005/0177240 A1 | 8/2005 | Blain | |
| 2006/0004367 A1 | 1/2006 | Alamin et al. | |
| 2006/0036243 A1 | 2/2006 | Sasso et al. | |
| 2006/0036323 A1 | 2/2006 | Carl et al. | |
| 2006/0149289 A1 | 7/2006 | Winslow et al. | |
| 2006/0190081 A1 | 8/2006 | Kraus et al. | |
| 2006/0276790 A1 | 12/2006 | Dawson et al. | |
| 2007/0027081 A1 | 2/2007 | Marx et al. | |
| 2007/0055245 A1 | 3/2007 | Sasso et al. | |
| 2007/0073290 A1 | 3/2007 | Boehm | |
| 2007/0213717 A1 | 9/2007 | Trieu et al. | |
| 2007/0213822 A1 | 9/2007 | Trieu | |
| 2007/0250166 A1 | 10/2007 | McKay | |
| 2007/0282445 A1 | 12/2007 | Reiley | |
| 2008/0058954 A1 | 3/2008 | Trieu | |
| 2008/0161810 A1 * | 7/2008 | Melkent | A61B 17/14 606/79 |
| 2009/0024166 A1 | 1/2009 | Carl et al. | |
| 2009/0054313 A9 | 2/2009 | Marx et al. | |
| 2009/0125066 A1 | 5/2009 | Kraus et al. | |
| 2009/0157119 A1 | 6/2009 | Hale | |
| 2009/0177205 A1 | 7/2009 | McCormack et al. | |
| 2009/0204152 A1 | 8/2009 | Blain | |
| 2009/0263319 A1 | 10/2009 | Wohabrebbi et al. | |
| 2009/0263321 A1 | 10/2009 | McDonald et al. | |
| 2009/0264928 A1 | 10/2009 | Blain | |
| 2010/0087923 A1 | 4/2010 | Abdou | |
| 2010/0114175 A1 | 5/2010 | McKay | |
| 2010/0119492 A1 | 5/2010 | Hans et al. | |
| 2010/0121378 A1 | 5/2010 | Malek | |
| 2010/0137910 A1 | 6/2010 | Cawley et al. | |
| 2010/0191241 A1 | 7/2010 | McCormack et al. | |
| 2010/0203102 A1 | 8/2010 | Wohabrebbi | |
| 2010/0211109 A1 | 8/2010 | Doerr | |
| 2010/0331891 A1 | 12/2010 | Culbert et al. | |

OTHER PUBLICATIONS

Goel et al., Craniovertebral instability due to degenerative osteoarthritis of the atlantoaxial joints: analysis of the management of 108 cases, Dept. of Neurosurgery, King Edward VII Memorial Hosp. and Seth G. S. Medical College, Parel, Mumbai, India, J. Neurosurg Spine 12:592-601, 2010.

Goel, Facet distraction spacers for treatment of degenerative disease of the spine: Rationale and an alternative hypothesis of spinal degeneration, Journal of Craniovertebral Junction & Spine, Dept. of Neurosurgery, King Edward VII Memorial Hosp. and Seth G. S. Medical College, Parel, Mumbai, India, J. Neurosurg Spine vol. 1, Issue 2, pp. 65-66, 2010.

* cited by examiner

METHODS AND INSTRUMENTS FOR USE IN VERTEBRAL TREATMENT

CROSS-REFERENCE TO RELATED APPLICATIONS

This application is a divisional application of U.S. patent application Ser. No. 13/098,026, filed on Apr. 29, 2011, which is incorporated herein by reference herein, in its entirety.

FIELD OF THE INVENTION

The present invention relates generally to the field of surgically treating one or more vertebrae. Treatment may include one or more manipulations, such as but not limited to, mobilizing, aligning, cutting, abrading, and preparing facet joints with instruments. Implants may be used in some embodiments to aid with or maintain the one or more manipulations. Some, but not all, treatments are specifically directed to manipulations of cervical vertebrae.

BACKGROUND

Facet joints and discs disposed between vertebral members permit motion between individual vertebral members. Each vertebra includes an anterior body and a posterior arch. The posterior arch includes two pedicles and two laminae that join together to form the spinous process. A transverse process is laterally positioned at the transition from the pedicles to the laminae. Both the spinous process and transverse processes provide for attachment of fibrous tissue, such as ligaments and muscle. Two inferior articular processes extend downward from the junction of the laminae and the transverse process. Further, two superior articular processes extend upward from the junction. The articular processes of adjacent vertebrae form the facet joints. The inferior articular process of one vertebra articulates with the superior articular process of the vertebra below. The facet joints are referred to as gliding joints because the articular surfaces glide over each other. As illustrated in FIG. 1, adjacent vertebrae V1, V2 have a disc D between their anterior bodies, and a facet joint FJ between articular processes. In the side elevation view of FIG. 1, only one of two bilateral facet joints FJ is shown. The spinal segment illustrated is a cervical spinal segment, but the present invention is not limited to treatment of the cervical spine. A foramen F, or opening, between adjacent vertebrae V1, V2 is typically occupied by nerves exiting from a spinal cord.

Vertebral manipulation and implants are often used in the surgical treatment of spinal disorders such as degenerative disc disease, disc herniation, curvature abnormalities, and trauma. FIG. 2 illustrates a spinal segment where inappropriate spacing between vertebrae V1, V2 has occurred as a result of some spinal disorder. The disc D and the facet joint FJ are shown in a compressed state and extending beyond their normal bounds. The foramen F is reduced in size by movement of the vertebrae V1, V2, and encroachment of disc and facet joint material. Reduction in the size of the foramen F may cause nerve compression and resultant pain and lack of nerve function. In some cases, spinal fusion is indicated to create appropriate spacing between vertebrae and to inhibit relative motion between vertebrae, thereby relieving nerve compression. Spinal fusion often involves the removal of the vertebral disc and insertion of an interbody implant to create a fused junction between a pair of vertebral bodies. Facet joints may be fused, including fusion with spacers, in conjunction with anterior vertebral bodies to complete the fusion between vertebrae. Facet joints may also be separately treated by fusion. Spinal fusion will be collective referred to herein to include one or both of anterior column vertebral body fusion and facet joint fusion. Facet fusion may be initiated by decorticating the opposing articulating surfaces and packing bone growth promoting substances or inserting implants into the spaces between the articular processes. Facet arthroplasty devices may also be implanted in facet joints after preparation of the facet joints. It may be difficult for a surgeon to determine the amount of contouring and shaping required for each of the articular processes. A trial-and-error routine may be performed as the surgeon removes a first amount of material from one or both surfaces and determines whether the spacing is adequate for receiving a fusion substance or device. An increased amount of precision is desirable for preparing the articulating surfaces to receive an implant or bone growth promoting substances. In some embodiments, such precision would minimize the possibility of producing excessive trauma and bone removal from the facets while optimizing the probability of improving or maintaining appropriate foraminal area and achieving a successful arthrodesis.

Spinal disc material is often detached and removed in association with spinal procedures such as discectomy, spinal fusion, and disc replacement. In these and other spinal procedures, facet joint or disc soft tissues have traditionally been detached and removed with grasping, clipping, cutting, and scraping instruments such as rongeurs, curettes, rasps, osteotomes, scrapers, burs, or sagittal saws. A shortcoming of many traditional instruments is a failure to provide limits to the movement and effective cutting zone of the instruments. Improved instruments and methods may increase patient safety and operational accuracy by incorporating limits to the movement and effective cutting zone of instruments.

Improved methods and instruments may also provide for one or more of instruments with leading edges configured to distract a space between bones into which they are inserted, and sizes and shapes that reflect the sizes and shapes of implants to be placed in a patient. Distraction instruments may be useful to properly space and align bones to be treated. Distraction instruments that also reflect the size and shape of implants to be placed in a patient provide for proper selection of implants without the need for an additional sizing instrument or template.

SUMMARY

One embodiment of the invention is a method of surgically treating vertebrae. The method may include separating vertebrae at one or more facet joints between the articular processes of the vertebrae, introducing an instrument into at least one of the one or more facet joints to remove tissue from one or more articular processes, and advancing the instrument until a stop on the instrument terminates advancement of the instrument by contacting a vertebra. The method may also include placing an implant into one or more facet joints.

Another embodiment of the invention is a method of surgically treating vertebrae. The method may include separating and removing tissue from vertebrae at one or more facet joints between articular processes of the vertebrae with a single instrument. The single instrument may be used to remove tissue from one or more articular processes by introducing the single instrument into one or more facet joints, and advancing the instrument until a stop on the instrument terminates advancement of the instrument by contacting a vertebra. The method may also include placing an implant into one or more facet joints.

Yet another embodiment of the invention is an instrument configured to remove tissue from a facet joint. Some embodiments include a body for use in controlling the placement of the instrument and a first cutting face coupled to the body and configured to be oriented toward a first articular process of the facet joint. Some embodiments include a stop that extends from the instrument such that the stop restricts advancement of the instrument into the facet joint at least in part by contacting a portion of a vertebra.

DETAILED DESCRIPTION

Figure 1:
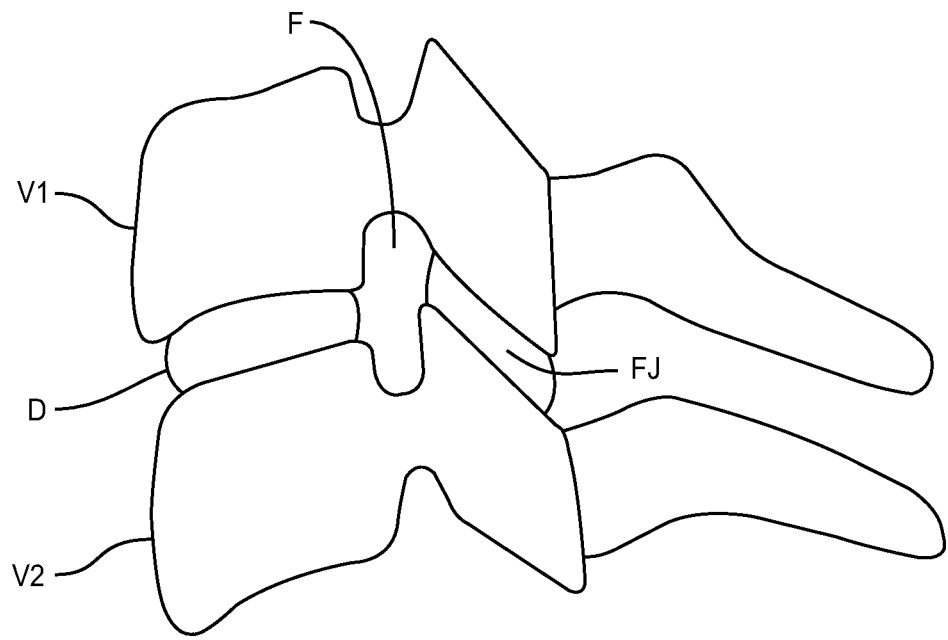
FIG. 1 is a side elevation view of a spinal segment.
Figure 2:
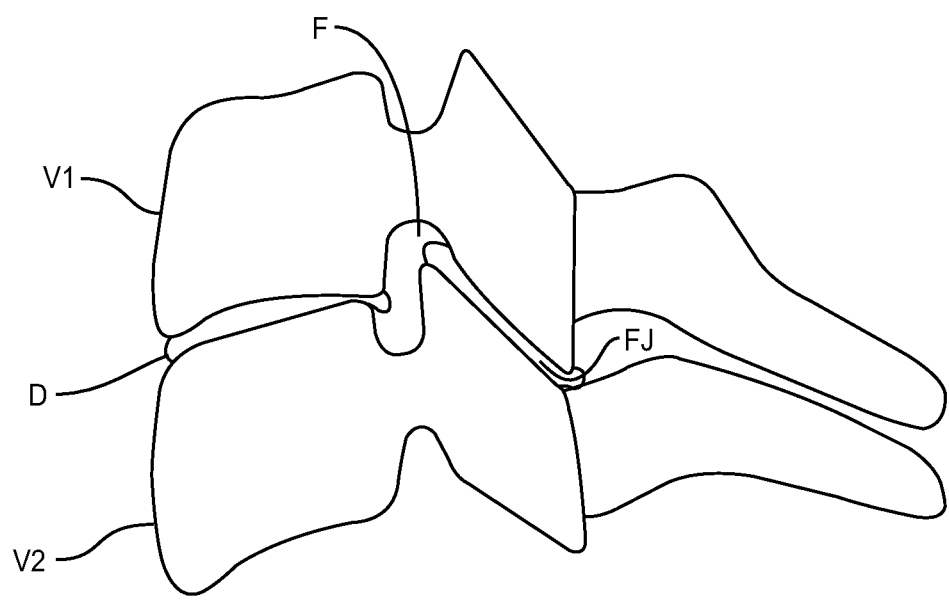
FIG. 2 is a side elevation view of a spinal segment depicting a spinal disorder.

An embodiment of a method of surgically treating vertebrae is illustrated in FIGS. 3-7. The discs D and facet joints FJ of FIGS. 1 and 2 have not been drawn in FIGS. 3-7, for clarity. In some embodiments, all or a part of the disc and facet joint material may be present while acts of the methods are performed. For example, tissue removal by instruments used during the methods may be employed to remove all or portions of the tissues of the synovial facet joints or all or portions of disc material, including but not limited to annulus, nucleus pulposis, and ligaments. All or a part of the disc and facet joint material may be removed prior to use of the instruments described in association with the method embodiments described. A state of spinal disorder is illustrated in FIG. 2. Inappropriate spacing between vertebrae V1, V2 is shown in FIG. 2. By comparison, the spinal segment illustrated in FIG. 1 presents appropriate spacing between vertebrae V1, V2. Disc and facet joint spacing are reduced, and the foramen F is reduced in size by movement of the vertebrae V1, V2. Reduction in the size of the foramen F may cause nerve compression and resultant pain and lack of nerve function.

Figure 3:
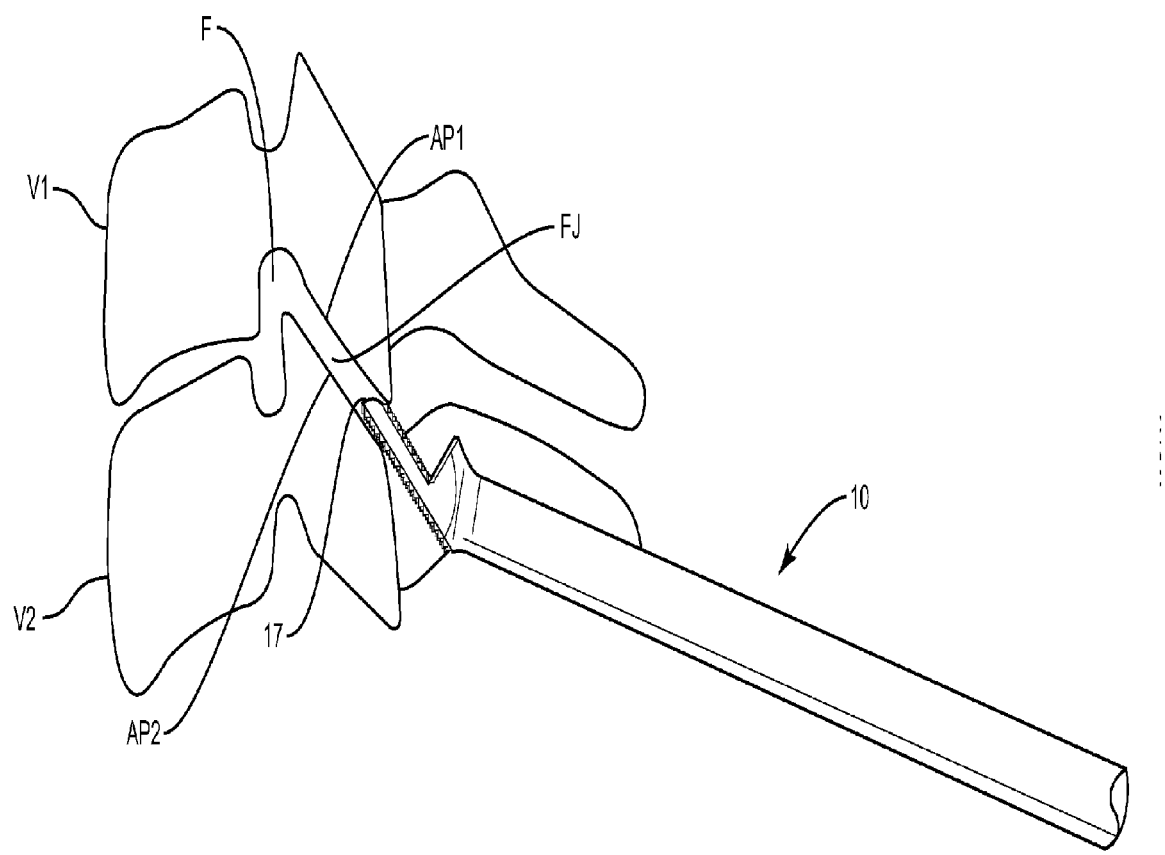
FIG. 3 is a side elevation view of an instrument being introduced into a spinal segment.
Figure 4:
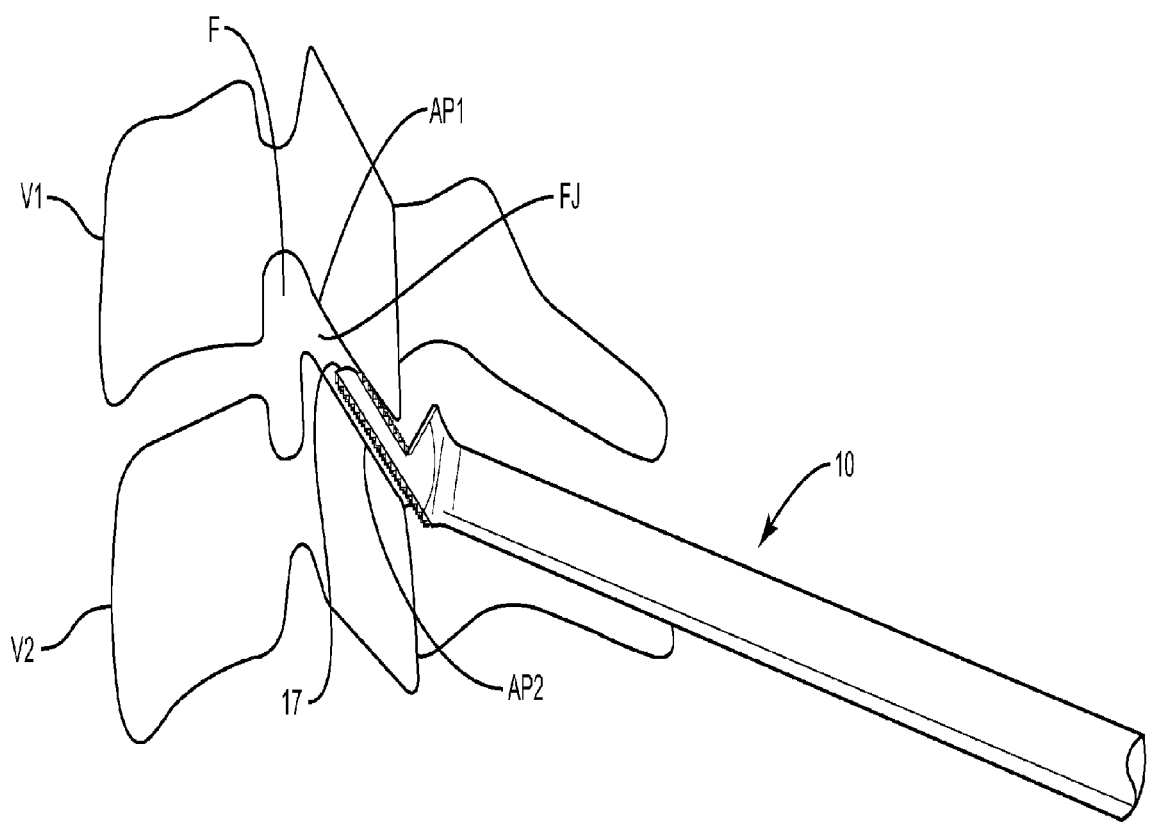
FIG. 4 is a side elevation view of an instrument being introduced into a spinal segment.

A separating action of the vertebrae V1, V2 is illustrated in FIGS. 3 and 4. Separation is being implemented with a first instrument 10. The first instrument 10 shown includes a self-distracting leading end 17. The self-distracting leading end 17 is configured to fit into a smaller space between the vertebrae V1, V2 and includes a curved incline that facilitates pushing apart of the vertebrae V1, V2 at the facet joint. The self-distracting leading end 17 has been inserted into the facet joint in FIG. 3 and has been used to push apart the vertebrae V1, V2 at their articular processes AP1, AP2, compared with the state of the vertebrae V1, V2 shown in FIG. 2. The self-distracting leading end 17 of the first instrument 10 is shown inserted further into the facet joint FJ in FIG. 4. Consequently, the vertebrae V1, V2 in FIG. 4 have been returned to an appropriate spacing. In the illustrated embodiment, this separation is shown being accomplished unilaterally with the first instrument 10 alone, but in other embodiments, return of vertebrae to an appropriate spacing may require multiple, sequentially larger instruments. Separation of vertebrae may be accomplished by any effective technique or with any effective device. For example and without limitation, separation of vertebrae may be accomplished with a wedge or bullet shaped instrument, including a wedge or bullet shaped tip on an instrument such as the first instrument 10. Separation may be accomplished with a separate spreader instrument like a lamina spreader or a spinous process spreader. A spreader of any effective type may be coupled with one or both of the vertebrae to be separated and operated to move the vertebrae apart. Separation of vertebrae may be accomplished by distraction off of other instrumentation, such as but not limited to, pedicle screw constructs, some of which may include spinal rods. Separation may be accomplished by contralateral distraction of the facet joints.

Figure 8:
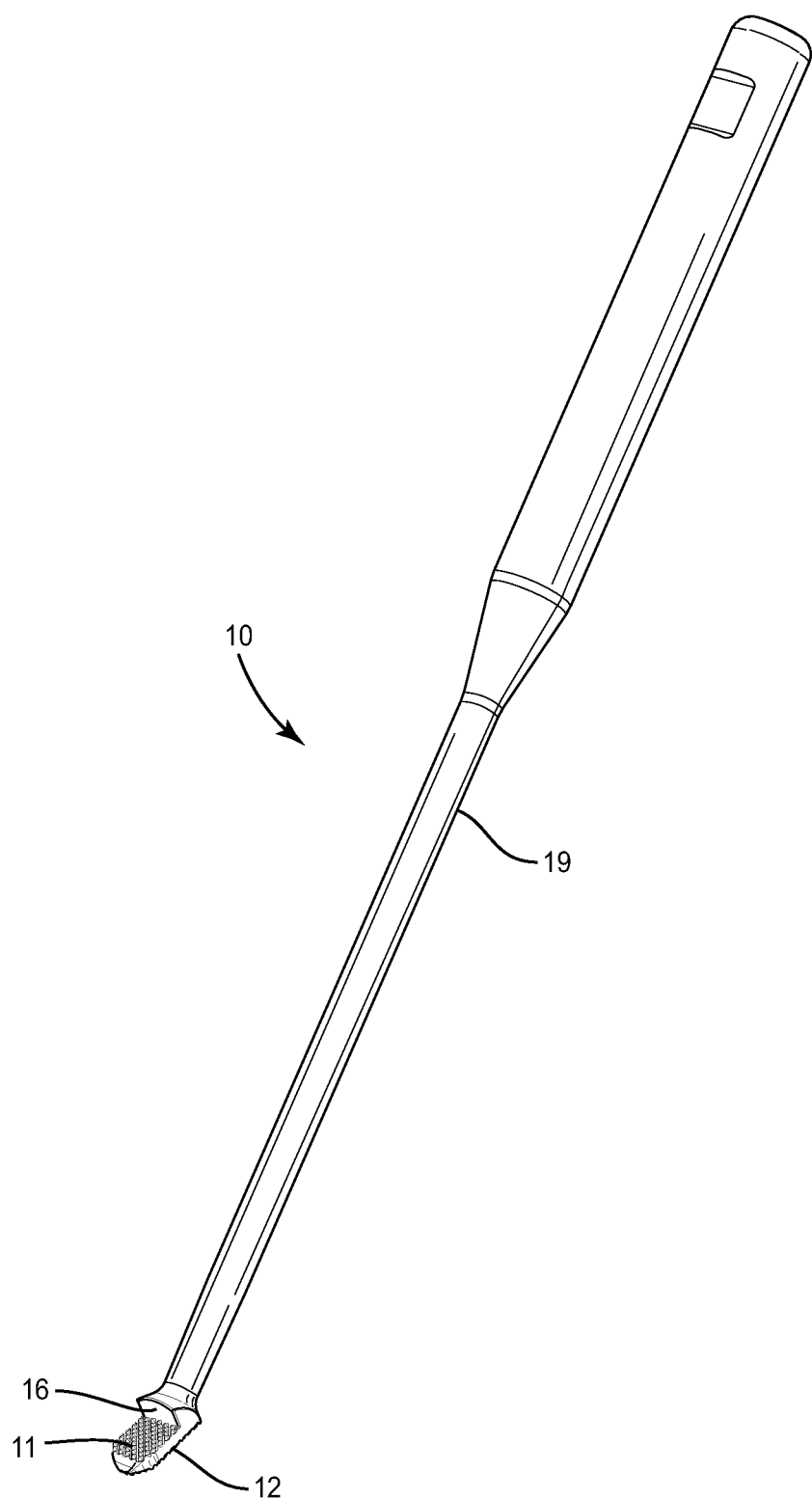
FIG. 8 is a perspective view of a spinal preparation instrument.
Figure 9:
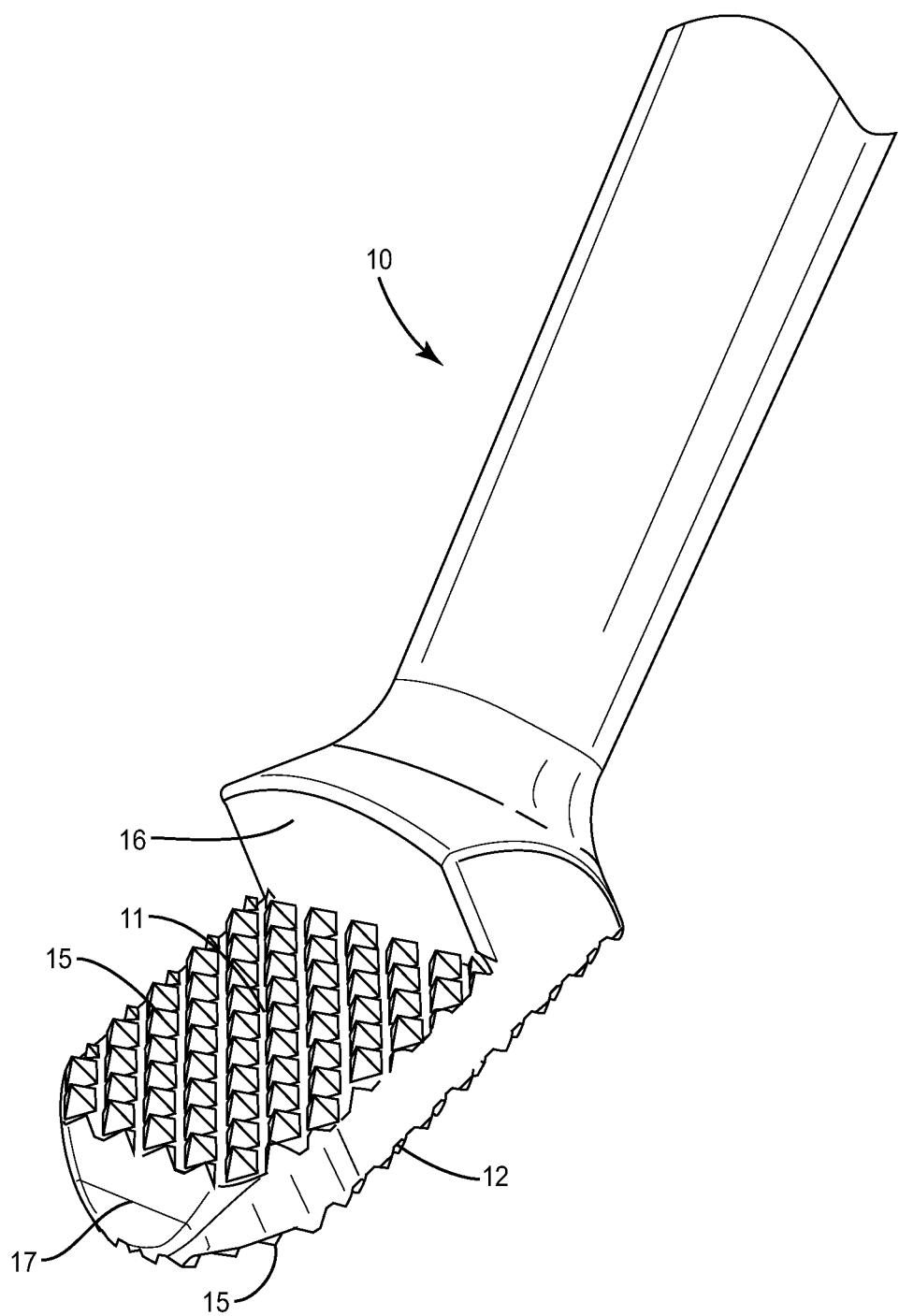
FIG. 9 is a more detailed perspective view of the spinal preparation instrument of FIG. 8.
Figure 10:
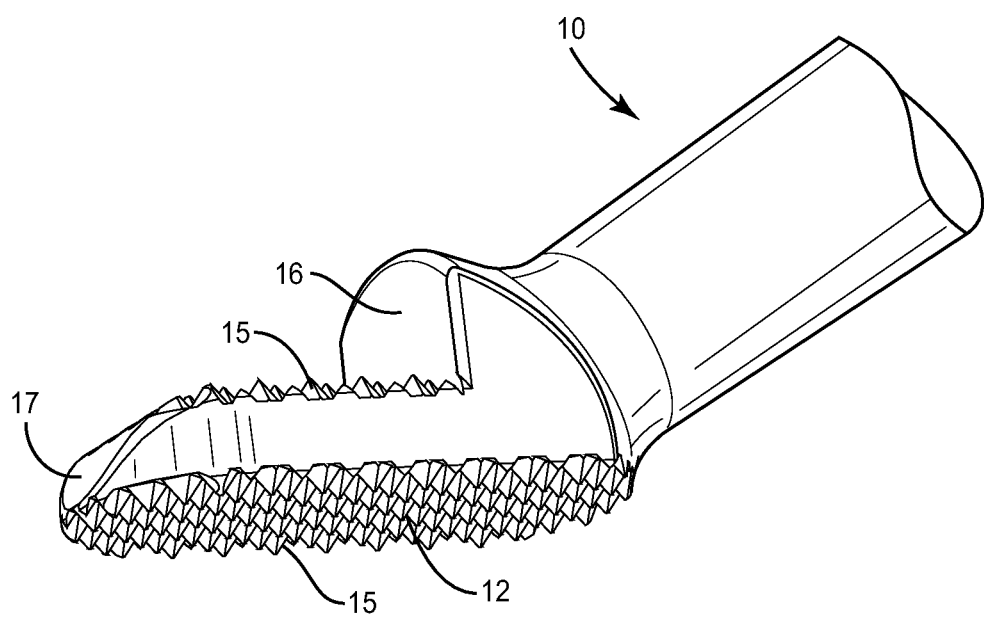
FIG. 10 is a more detailed perspective view of the spinal preparation instrument of FIG. 8.
Figure 11:
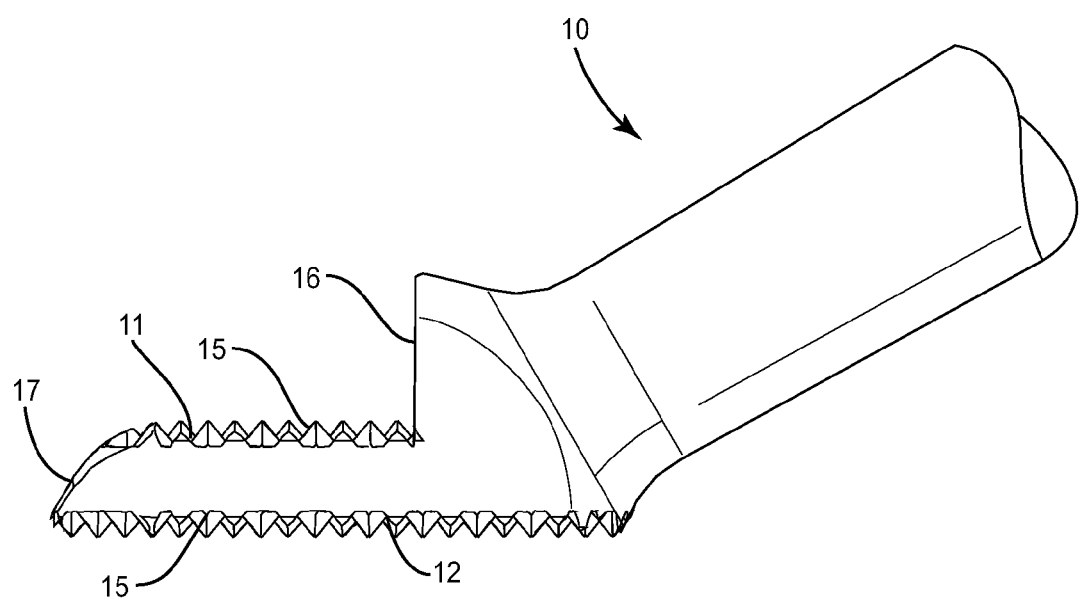
FIG. 11 is a more detailed perspective view of the spinal preparation instrument of FIG. 8.
Figure 12:
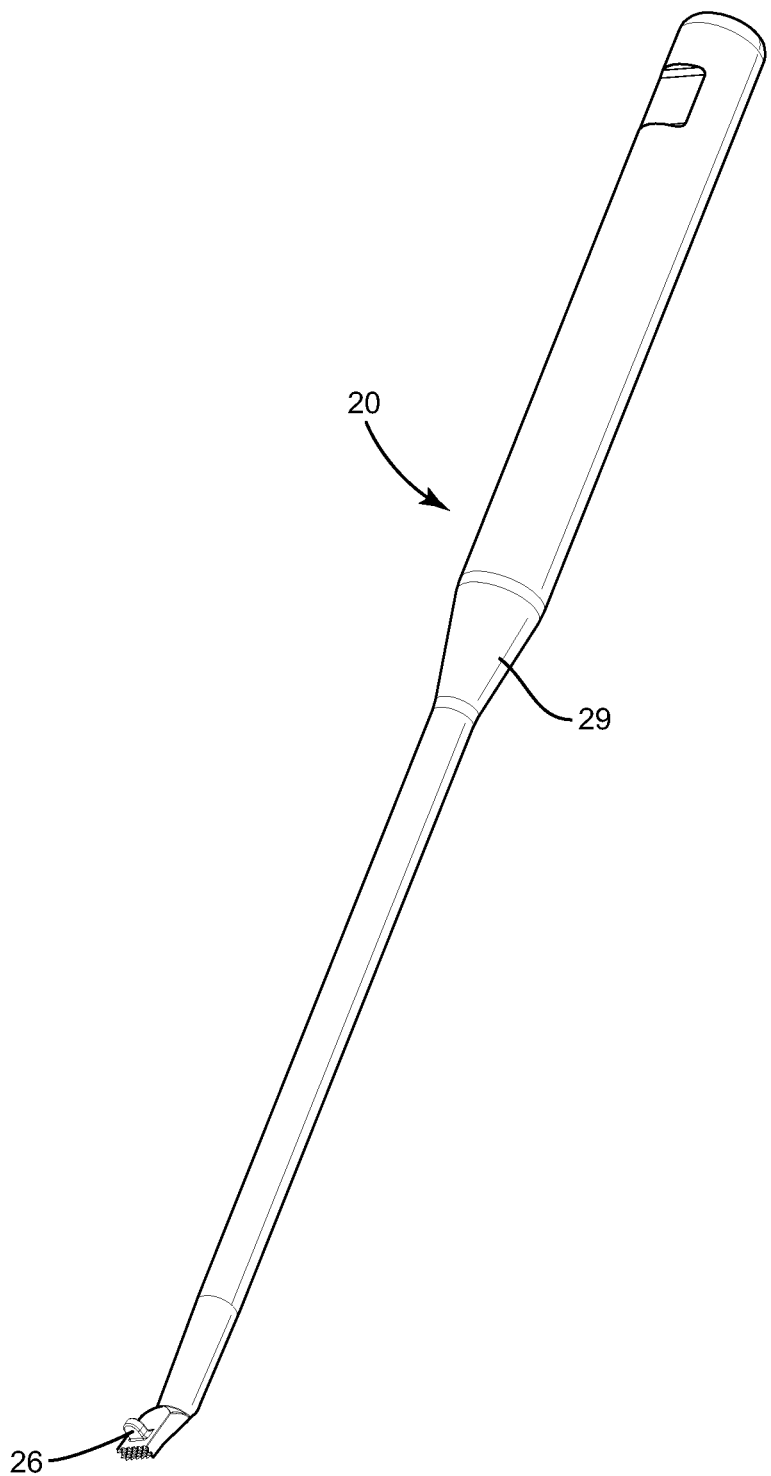
FIG. 12 is a perspective view of a spinal implant pusher instrument.

The first instrument 10 illustrated in FIGS. 3-5 and 8-11 is introduced into the facet joint FJ to remove tissue from the articular processes AP1, AP2. The first instrument 10 shown includes rasp teeth 15 on first and second cutting faces 11, 12 (FIGS. 9-11). The act of introducing the instrument 10 into the facet joint FJ causes tissue to be removed from the articular processes, including but not limited to, removal of cartilaginous and connective tissue from surfaces of the articular processes. Introduction of the instrument 10 may include reciprocating motions or other motions effective to remove additional tissue. In some embodiments, cutting faces may include other types of blades, abrasives, or cutters. For example and without limitation, the cutting faces may include grating teeth, a single blade, multiple blades, blades at common angles and orientations with respect to the faces, blades at differing angles and orientations with respect to the faces, spikes, cutting wires, and other abrasive surfaces. Tissue removed may include bone or the soft tissue present, such as the soft tissue of the facet joints.

Other embodiments may employ an instrument with a cutting area, such as the first and second cutting faces 11, 12, on only one face of the instrument. Such an instrument may be useful to remove material or shape a selected one of the articular processes while continuing to guide and space relative to the other articular process.

Figure 5:
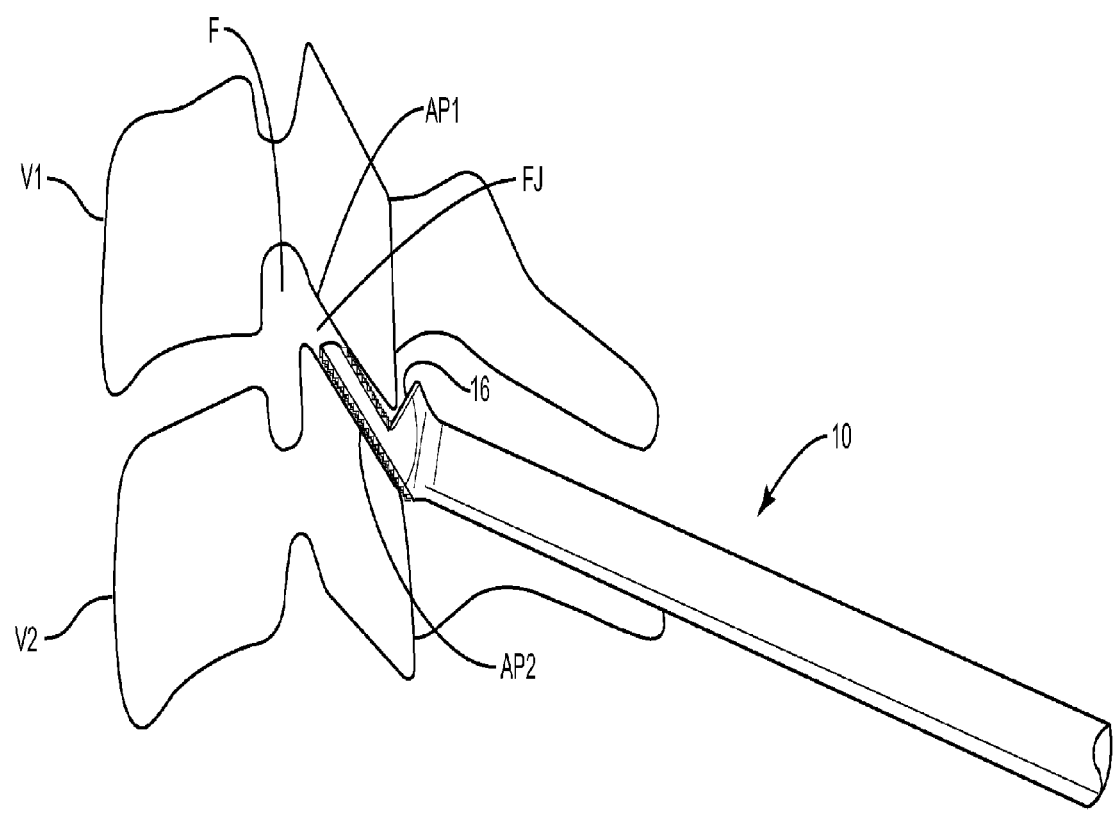
FIG. 5 is a side elevation view of an instrument being introduced into a spinal segment.

In FIG. 5, an act of advancing the first instrument 10 until a stop 16 (FIGS. 5 and 9-11) on the first instrument 10 terminates advancement of the first instrument 10 by contacting the vertebra V1 is shown. The illustrated stop 16 extends substantially perpendicularly from the first cutting face 11 and is configured to contact a portion of the vertebra V1, which is the superior vertebra in the illustrated spinal segment. In other embodiments, a stop may be configured to contact an inferior vertebra such as V2, multiple portions of a vertebra, multiple vertebrae, or other anatomical structures to terminate advancement of an instrument. A stop may be of any effective geometry to terminate advancement of an instrument.

The first instrument 10 of the illustrated embodiment is a single instrument used to both separate the vertebrae V1, V2 and to remove tissue from one or more of the articular processes. For some method embodiments, a set of two or more progressively larger instruments that both separate vertebrae and remove tissue from articular processes may be provided. A description of a single instrument is intended to describe one instrument that both separates and removes tissue and is not intended to limit supplying of instruments in a set. In some embodiments, separate instruments may be used to separate vertebrae and to remove tissue. Sets of separate instruments of differing size may be employed in some embodiments. One or both of separating and tissue removing instruments may also be sizing instruments for implants to be placed into one or more facet joints. By also making separating and tissue removing instruments sizing instruments, a proper size and location for an implant may be established without the need of placing separate sizing trials, templates, or other measuring devices. For example and without limitation, the first instrument 10 shown in FIG. 5 is of the same size and shape as implant 30 shown in FIGS. 6 and 7. Alternate embodiments may include use of a more traditional set of separate sizers.

Figure 6:
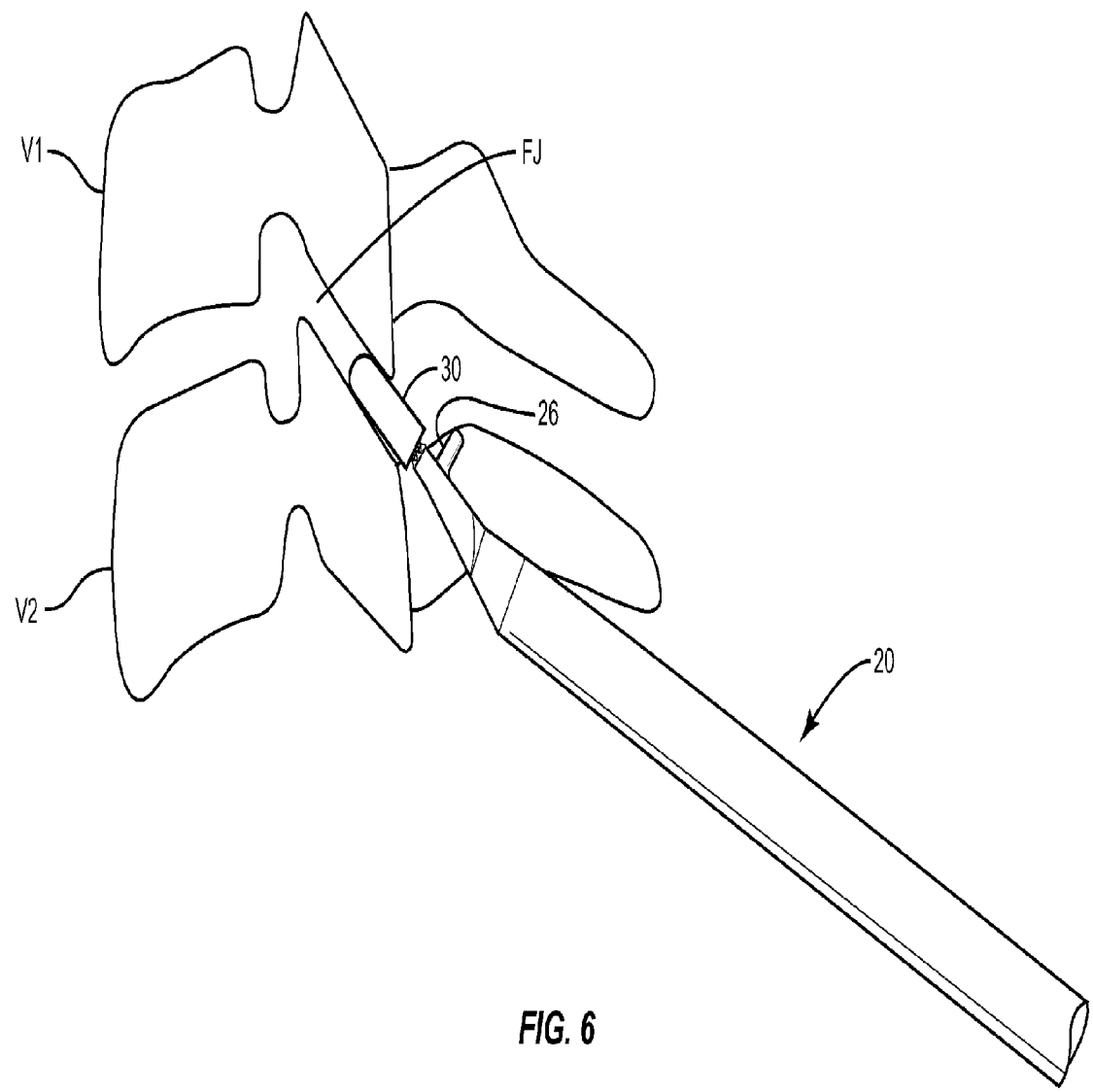
FIG. 6 is a side elevation view of an instrument being used to advance an implant into a spinal segment.
Figure 7:
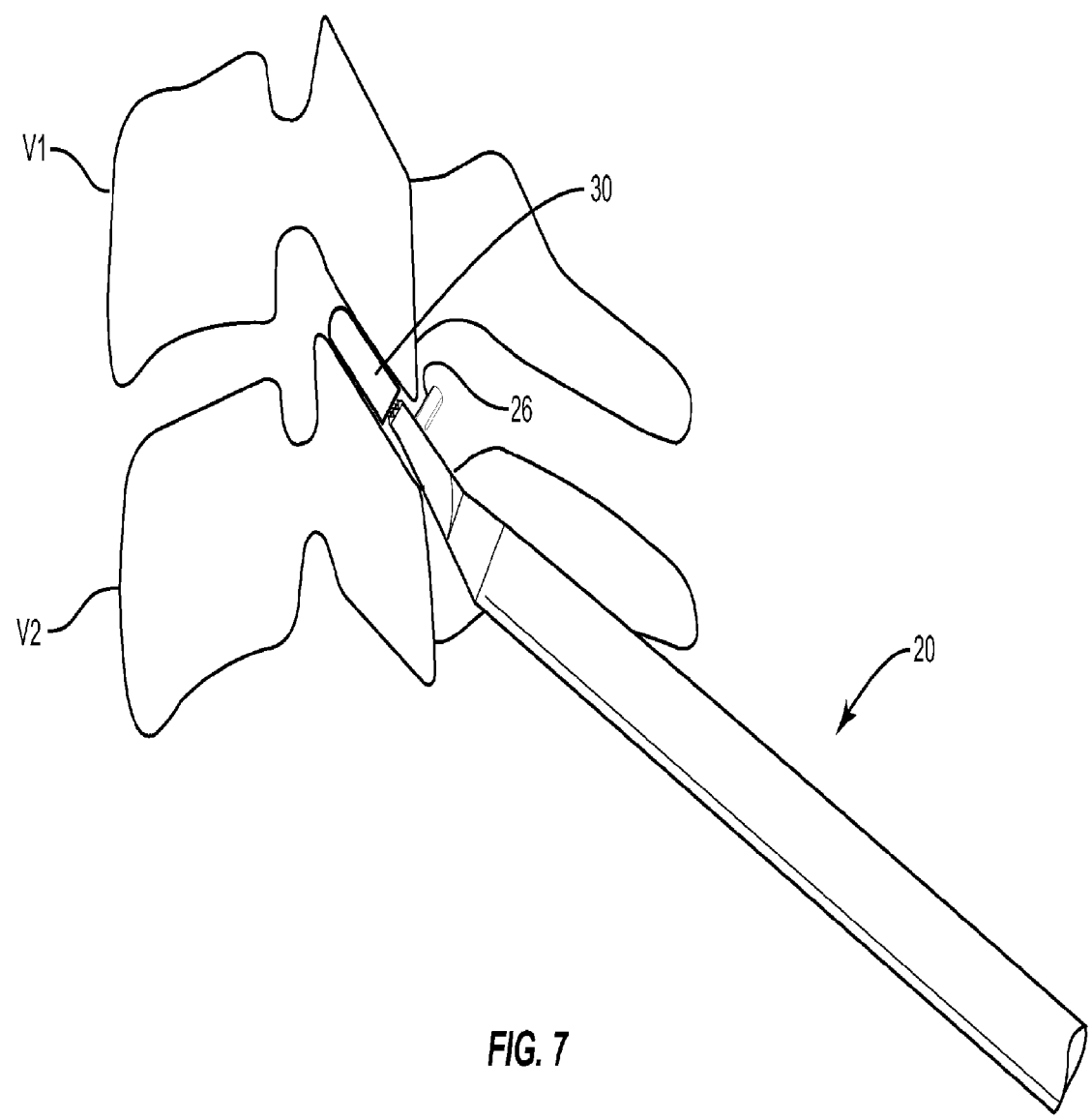
FIG. 7 is a side elevation view of an instrument being used to advance an implant into a spinal segment.

Some method embodiments include placing an implant into one or more of the facet joints FJ. Insertion of an implant 30 is shown in FIGS. 6 and 7. In FIG. 6, a second instrument 20, which is a pusher instrument, is shown contacting the implant 30 and advancing the implant 30 into a facet joint FJ. The vertebrae V1, V2 are shown being held in a distracted state in FIGS. 6 and 7. Distraction may be accomplished by any effective method, including contralateral distraction with the first instrument 10. In other embodiments, the implant 30 may be self-distracting and be inserted into a facet joint that is not being held in a distracted state. For example, the implant 30 of some embodiments may be used alone or in combination with instruments to fully or partially transform the vertebrae V1, V2 from a collapsed state to a distracted state, as shown in the vertebral positions of the vertebrae V1, V2 in FIGS. 2 through 4. The second instrument 20 includes a pusher stop 26 on the second instrument 20 that terminates advancement at least in part by contacting a portion of the vertebra V1, as shown in FIG. 7. The illustrated pusher stop 26 extends substantially perpendicularly from a core portion of the second instrument 20 and is configured to contact a portion of the vertebra V1, which is the superior vertebra in the illustrated spinal segment. In other embodiments, a pusher stop may be configured to contact an inferior vertebra such as the vertebra V2, multiple portions of a vertebra, multiple vertebrae, or other anatomical structures to terminate advancement of an instrument. A pusher stop may be of any effective geometry to terminate advancement of an instrument.

A more detailed depiction of the first instrument 10 is provided in FIGS. 8-11. The first instrument 10 is configured to remove tissue from a facet joint. The illustrated first instrument 10 includes a body 19 for use in controlling the placement of the first instrument 10. The body 19 shown includes a shaft and a handle that may be grasped to control the placement and positioning of the first instrument 10. In some embodiments, a body may include mechanisms for coupling to other devices that are capable of moving the instrument in a controlled way or stabilizing the instrument.

A first cutting face 11 is illustrated in FIGS. 8, 9, and 11. What is specified as a first cutting face here may be located on any side of the first instrument 10 in other embodiments. The first cutting face 11 shown is coupled to the body 19 and configured to be oriented toward a first articular process AP1 of a facet joint FJ (FIGS. 3-5). The first cutting face 11 includes rasp teeth 15. The rasp teeth 15 shown are pyramid shaped. Rasp teeth may be of any effective shape to cut tissue. Rasp teeth may cut in response to motion in any direction or may be angled to limit their cutting to only movements in certain directions. In some embodiments, a cutting face may include another type of cutting mechanism. For example and without limitation, a cutting face may include one or more blades, abrasives, grating mechanisms, spikes, wires, fixed cutters, rotary cutters, reciprocating cutters, or other mechanisms capable of cutting.

The first instrument 10 illustrated in FIGS. 8-11 includes a second cutting face 12 coupled to the body 19 and oriented toward a second articular process AP2 of the facet joint FJ (FIGS. 3-5) when the first cutting face 11 is oriented toward the first articular process AP1. The second cutting face 12 includes rasp teeth 15. The rasp teeth 15 shown are pyramid shaped. As with the first cutting surface 11, the second cutting face 12 may include any mechanisms effective to cut tissue.

As shown in FIGS. 8-11, the stop 16 extends from the first instrument 10. The stop 16 restricts advancement of the first instrument 10 into the facet joint at least in part by contacting a portion of the first vertebra V1 (FIG. 5). More particularly, the stop 16 shown extends substantially perpendicularly from the first cutting face 11. In other embodiments, a stop may extend from the second cutting face 12, or some other portion of the instrument. Multiple stops may extend from multiple portions of the instrument. By way of non-limiting example, stops may be configured to extend from each of the first cutting face 11 and the second cutting face 12 such that advancement of the first instrument 10 would be stopped by contact with either or both of the first and second vertebrae V1, V2. A stop may be of any effective geometry to terminate advancement of an instrument.

The self-distracting leading end 17 of the first instrument 10 is illustrated in FIGS. 3, 4, and 9-11. The self-distracting leading end 17 shown includes a curved incline that is more curved near the first cutting face 11 than the second cutting face 12. Other embodiments of a self-distracting leading end may include any shape or mechanism that permits the instrument to enter and push apart portions of opposing vertebrae. For example and without limitation, a self-distracting leading end may be bullet shaped, in the shape of a wedge, have curved surfaces, straight surfaces, or combinations of curved and straight surfaces, including surfaces with differing rates and directions of curvature. The self-distracting leading end 17 is configured to separate vertebrae from each other when the leading end 17 is introduced into a facet joint. By way of non-limiting example, the self-distracting leading end 17 of the first instrument 10 is shown separating vertebrae V1, V2 when the self-distracting leading end 17 is introduced into the facet joint FJ in FIGS. 3 and 4.

The first instrument 10 may also be used as a sizer to assist with the selection of an implant to be place in the facet joint from which tissue is removed. A set of two or more progressively larger instruments, such as the first instrument 10, may be provided. By making such instruments sizing instruments, a proper size and location for an implant may be established without providing separate sizing trials, templates, or other measuring devices. For example and without limitation, the first instrument 10 shown in FIG. 5 is of the same size and shape as the implant 30 shown in FIGS. 6 and 7.

The second instrument 20, also described as a pusher instrument herein, is shown in FIGS. 6, 7, 12, and 13. The second instrument 20 includes a body 29, an implant interface 21 coupled to the body 29, and a pusher stop 26 that extends substantially perpendicularly from a core portion of the second instrument 20. The implant interface 21 illustrated in FIG. 13 includes teeth 25. The teeth 25 shown are pyramid shaped to create frictional engagement between an implant and the second instrument 20. An implant interface may include any surface or mechanism designed to create friction or grasping force between an implant and an instrument. For example and without limitation, an implant interface may include one or more of notches, teeth, screws, blades, abrasives, spikes, and wires. The illustrated pusher stop 26 is configured to contact a portion of the vertebra V1, which is the superior vertebra in the illustrated spinal segment (FIG. 7). In other embodiments, a pusher stop may extend from any other portion of the instrument. Multiple pusher stops may extend from multiple portions of the instrument. For example, in some embodiments, advancement of a second instrument could be stopped by contact with either or both of the first and second vertebrae V1, V2. A pusher stop may be of any effective geometry to terminate advancement of an instrument.

Figure 13:
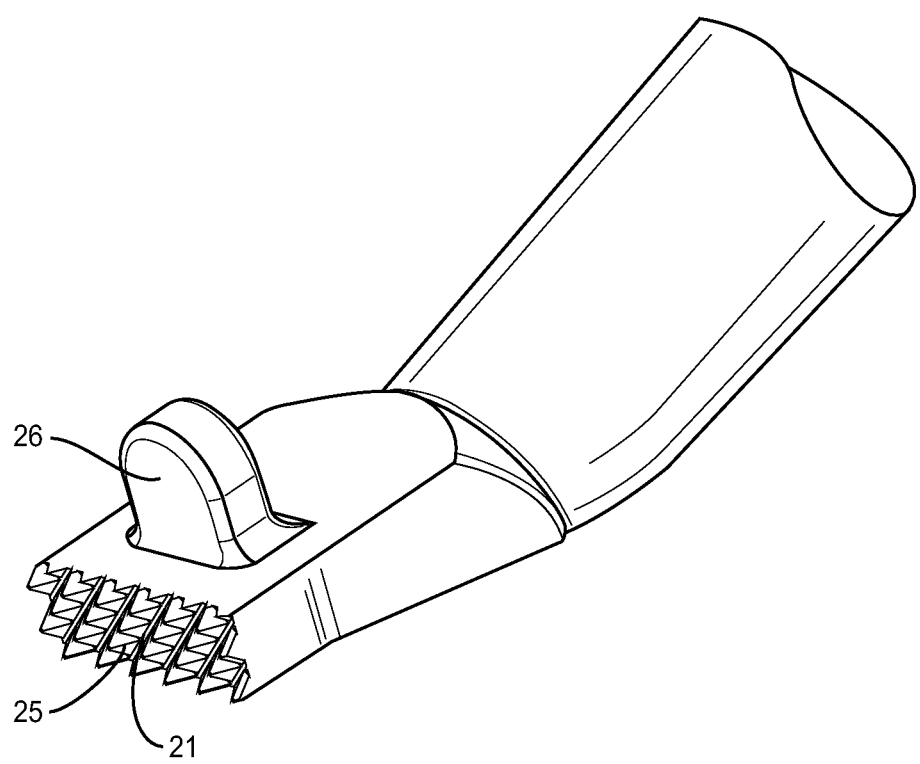
FIG. 13 is a more detailed perspective view of the spinal implant pusher instrument of FIG. 12.
Figure 14:
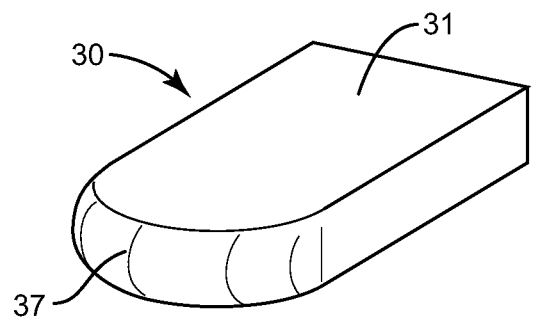
FIG. 14 is a perspective view of a spinal implant.
Figure 15:
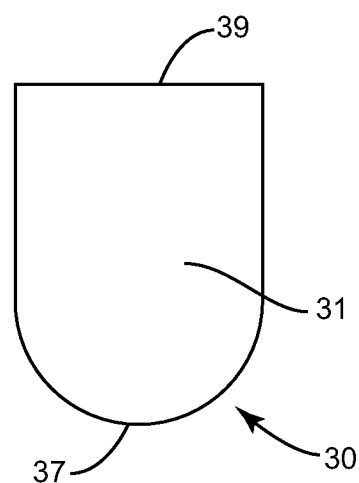
FIG. 15 is a top plan view of the spinal implant of FIG. 14.
Figure 16:
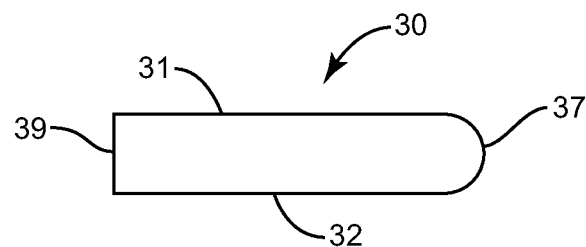
FIG. 16 is a side elevation view of the spinal implant of FIG. 14.

The implant 30 shown in FIGS. 6, 7, and 14-16 includes a curved leading end 37 and a trailing end 39 configured to be pushed by the second instrument 20. The curved leading end 37 may facilitate insertion between vertebrae. The illustrated curved leading end 37 is curved both side-to-side and between a top surface 31 and a bottom surface 32. Some embodiments of a curved leading end may be curved only in one direction or may be curved in a compound manner. The trailing end 39 shown is configured to match the implant interface 21 (FIG. 13). Any other shaped trailing end that is effective to be pushed into place is contemplated. The top surface 31 and the bottom surface 32 may include surface preparations to increase friction and reduce motion between the implant 30 and the vertebrae against which the implant 30 is finally positioned. The surface preparations may include any coating or alteration, such as but not limited to, teeth, ridges, knurling, cuts, openings, cross-hatching, and roughening.

The implant may be of any effective size to be inserted between and space apart vertebrae at facet joints. For example and without limitation, the top and bottom surfaces 31, 32 may be approximate 8 mm by 8 mm. The implants 30 may come in a variety of heights, such as but not limited to, 2 mm, 3 mm, 4 mm, 5 mm, and 6 mm Other effective sizes, shapes, and configurations are contemplated. An implant may include one or more openings partially or completely through the implant. In some embodiments, the implant 30 is made from allograft bone. The implant 30 may also be made from autograft, or xenograft bone, ceramics, shape-memory alloys, titanium, titanium alloys, cobalt chrome alloys, stainless steel, non-reinforced polymers, carbon-reinforced polymer composites, PEEK and PEEK composites, low density polyethylene, and combinations of these materials. A fill material may be introduced at a surgical site in combination with an implant. The fill material may be a paste, gel, liquid, suspension, granular mixture, or similar substance. Non-limiting examples of fill materials include bone paste, morselized allograft, autograft, or xenograft bone, ceramics, or various polymers. The fill material may be a material that hardens after implantation. Some fill materials which are not necessarily hardenable or curable may be used in association with the present invention. For example, the fill material may comprise beads or small particles or grains of material, some of which may, in aggregate, achieve a harder consistency as a result of interlocking or compaction. In some embodiments, the fill material may also include a bone growth promoting substance. Osteogenic or bone growth promoting substances may include, without limitation, autograft, allograft, xenograft, demineralized bone, synthetic and natural bone graft substitutes, such as bioceramics and polymers, and osteoinductive factors. A separate carrier to hold materials within or near the device may also be used. These carriers may include collagen-based carriers, bioceramic materials, such as BIO-GLASS®, hydroxyapatite and calcium phosphate compositions. The carrier material may be provided in the form of a sponge, a block, folded sheet, putty, paste, graft material or other suitable form. The osteogenic compositions may include an effective amount of a bone morphogenetic protein (BMP), transforming growth factor $\beta 1$, insulin-like growth factor, platelet-derived growth factor, fibroblast growth factor, LIM mineralization protein (LMP), and combinations thereof or other therapeutic or infection resistant agents, separately or held within a suitable carrier material.

Embodiments of the instrument described herein may be constructed in whole or in part of biocompatible materials of various types. Examples of materials include, but are not limited to, shape-memory alloys, titanium, titanium alloys, cobalt chrome alloys, stainless steel, non-reinforced polymers, carbon-reinforced polymer composites, PEEK and PEEK composites, low density polyethylene, ceramics and combinations thereof.

Various method embodiments of the invention are described herein with reference to particular instruments and implants. However, in some circumstances, each disclosed method embodiment may be applicable to each of the instruments and implants, or to some other instrument or implant operable as disclosed with regard to the various method embodiments.

Terms such as anterior, posterior, top, bottom, side, lateral, and the like have been used herein to note relative positions. However, such terms are not limited to specific coordinate orientations, but are used to describe relative positions referencing particular embodiments. Such terms are not generally limiting to the scope of the claims made herein.

While embodiments of the invention have been illustrated and described in detail in the disclosure, the disclosure is to be considered as illustrative and not restrictive in character. All changes and modifications that come within the spirit of the invention are to be considered within the scope of the disclosure.

What is claimed is:

1. An instrument configured to remove tissue from a facet joint comprising:
    a body for use in controlling the placement of the instrument;
    a first cutting face coupled to the body and configured to be oriented toward a first articular process of the facet joint;
    a stop that extends from the instrument configured to restrict advancement of the instrument into the facet joint at least in part by contacting a portion of a vertebra; and a second cutting face coupled to the body and configured to be oriented toward a second articular process of the facet joint when the first cutting face is oriented toward the first articular process;
wherein a longitudinal axis defined by the stop intersects the second cutting face.

2. The instrument of claim 1, wherein the stop extends from the first cutting face.

3. The instrument of claim 1, further comprising a self-distracting leading end configured to separate vertebrae from each other when the leading end is introduced into the facet joint.

4. The instrument of claim 1, wherein the first cutting face comprises a plurality of rasp teeth.

5. The instrument of claim 1, wherein the stop extends from the first cutting face such that the stop extends perpendicular relative to the first cutting face.

6. The instrument of claim 1, wherein the first cutting face extends parallel to the second cutting face.

7. The instrument of claim 1, wherein the first and second cutting faces each comprise a plurality of rasp teeth.

8. The instrument of claim 7, wherein the rasp teeth are pyramid shaped.

9. The instrument of claim 1, wherein the first cutting face has a maximum length that is greater than that of the second cutting face.

10. The instrument of claim 1, further comprising a self-distracting leading end positioned between the first and second cutting faces configured to separate vertebrae from each other when the leading end is introduced into the facet joint.

11. The instrument of claim 10, wherein the self-distracting leading end includes a curved incline.

12. The instrument of claim 10, wherein the self-distracting leading end includes a curved incline that is more curved near the first cutting face than the second cutting face.

13. The instrument of claim 10, wherein the first and second cutting faces each comprise a plurality of rasp teeth and the self-distracting leading end and the stop are each smooth and free of any protrusions.

14. The instrument of claim 1, wherein the instrument comprises opposite first and second lateral surfaces extending between the first and second cutting faces, the first and second lateral surfaces being smooth and free of any protrusions.

15. A method for surgically treating vertebrae, comprising:
providing the instrument recited in claim 1, wherein the second cutting face is opposite the first cutting face and the instrument comprises a self-distracting leading end positioned between the first and second cutting faces;
separating vertebrae at one or more facet joints between articular processes of the vertebrae;
introducing the self-distracting leading end into at least one of the one or more facet joints to remove tissue from one or more articular processes;
advancing the instrument until the stop contacts a vertebra.

16. The method of claim 15, wherein the self-distracting leading end has a curved incline that is more curved near the first cutting face than the second cutting face.

17. The method of claim 15, further comprising placing an implant into one or more of the facet joints using a pusher instrument with a stop on the pusher instrument that terminates advancement at least in part by contacting a portion of the vertebrae.

18. An instrument configured to remove tissue from a facet joint comprising:
a body for use in controlling the placement of the instrument;
a first cutting face coupled to the body and configured to be oriented toward a first articular process of the facet joint, the first cutting face comprising a plurality of rasp teeth;
a second cutting face coupled to the body and positioned opposite the first cutting face, the second cutting face extending parallel to the first cutting face and configured to be oriented toward a second articular process of the facet joint when the first cutting face is oriented toward the first articular process, the second cutting face comprising a plurality of rasp teeth;
opposite first and second lateral surfaces extending between the first and second cutting faces, the first and second lateral surfaces being smooth and free of any protrusions;
a stop that extends from the first cutting face such that the stop extends perpendicular relative to the first cutting face, the stop being configured to restrict advancement of the instrument into the facet joint at least in part by contacting a portion of a vertebra, the stop being smooth and free of any protrusions, a longitudinal axis defined by the stop intersecting the second cutting face; and
a self-distracting leading end positioned between the first and second cutting faces and between the first and second lateral surfaces, the self-distracting leading end being configured to separate vertebrae from each other when the leading end is introduced into the facet joint, the self-distracting leading end being smooth and free of any protrusions, the self-distracting leading end having a curved incline that is more curved near the first cutting face than the second cutting face.

* * * * *

UNITED STATES PATENT AND TRADEMARK OFFICE
CERTIFICATE OF CORRECTION

PATENT NO. : 9,504,480 B2  
APPLICATION NO. : 14/617283  
DATED : November 29, 2016  
INVENTOR(S) : Marik et al.

Page 1 of 1

It is certified that error appears in the above-identified patent and that said Letters Patent is hereby corrected as shown below:

In the Specification

In Column 1, Lines 8-9, delete "Apr. 29, 2011, which" and insert -- Apr. 29, 2011, now Pat. No. 8,998,905, which --, therefor.

In Column 3, Line 59, delete "pulposis," and insert -- pulposus, --, therefor.

In Column 7, Line 53, delete "6mm Other" and insert -- 6mm. Other --, therefor.

Signed and Sealed this  
Seventh Day of February, 2017

Michelle K. Lee  
*Director of the United States Patent and Trademark Office*